(12) United States Patent
Roy

(10) Patent No.: US 8,306,613 B2
(45) Date of Patent: Nov. 6, 2012

(54) IRRITATION-REDUCING OCULAR IONTOPHORESIS DEVICE

(75) Inventor: Pierre Roy, Paris (FR)

(73) Assignee: EyeGate Pharma S.A.S. (FR)

( * ) Notice: Subject to any disclaimer, the term of this patent is extended or adjusted under 35 U.S.C. 154(b) by 0 days.

(21) Appl. No.: 13/218,006

(22) Filed: Aug. 25, 2011

(65) Prior Publication Data

US 2011/0306923 A1    Dec. 15, 2011

Related U.S. Application Data

(63) Continuation of application No. 13/042,529, filed on Mar. 8, 2011, which is a continuation of application No. 12/437,820, filed on May 8, 2009, now Pat. No. 7,937,142, which is a continuation of application No. 11/651,150, filed on Jan. 8, 2007, now Pat. No. 7,548,778, which is a continuation of application No. 10/861,117, filed on Jun. 3, 2004, now Pat. No. 7,164,943.

(30) Foreign Application Priority Data

Apr. 30, 2004 (FR) ...................... 04 04673

(51) Int. Cl.
*A61N 1/30* (2006.01)
(52) U.S. Cl. ........................................................ 604/20
(58) Field of Classification Search ................. 604/20, 604/890.1, 19, 501, 521, 289, 294; 607/53, 607/54, 141; 424/427
See application file for complete search history.

(56) References Cited

U.S. PATENT DOCUMENTS

| | | | |
|---|---|---|---|
| 551,880 A | 12/1895 | Wilcox | |
| 4,474,570 A * | 10/1984 | Ariura et al. | 604/20 |
| 4,678,466 A | 7/1987 | Rosenwald | |
| 4,752,285 A | 6/1988 | Petelenz et al. | |
| 4,955,378 A | 9/1990 | Grasso | |
| 5,053,000 A | 10/1991 | Booth et al. | |
| 5,053,001 A | 10/1991 | Reller et al. | |

(Continued)

FOREIGN PATENT DOCUMENTS

EP    0240189    10/1987

(Continued)

OTHER PUBLICATIONS

Sarraf et al., "The Role of Iontophoresis in Ocular Drug Delivery," Journal of Ocular Pharmacology; vol. 10, No. 1, 1994, pp. 69-81.

(Continued)

*Primary Examiner* — Manuel Mendez
(74) *Attorney, Agent, or Firm* — Pierce Atwood LLP; Joseph M. Maraia

(57) ABSTRACT

The invention provides an ocular iontophoresis device for delivering medication, the device comprising a medication reservoir suitable for being positioned on the eye, at least one medication in solution in the reservoir, an active electrode disposed in the reservoir, and a passive electrode, the device including at least one medication dissolved in non-saline water, the said solution having a pH lying in the range 6.5 to 8.5, the medication having a pKa lying in the range about 5.5 to about 9.5 and includes an active principle which is associated with an additive, such as a dendrimer, a polymer, a nanoparticle, a microsphere, a liposome, or an emulsion, and having an ionic form of valency greater than or equal to 1.

9 Claims, 4 Drawing Sheets

U.S. PATENT DOCUMENTS

| | | | |
|---|---|---|---|
| 5,174,304 | A | 12/1992 | Latina et al. |
| 5,420,109 | A | 5/1995 | Suto et al. |
| 5,472,436 | A | 12/1995 | Fremstad |
| 5,879,323 | A | 3/1999 | Henley |
| 6,001,088 | A | 12/1999 | Roberts |
| 6,154,671 | A * | 11/2000 | Parel et al. .................. 604/20 |
| 6,327,496 | B1 * | 12/2001 | Hamlin et al. ................ 604/20 |
| 7,164,943 | B2 | 1/2007 | Roy |
| 7,548,778 | B2 | 6/2009 | Roy |
| 2002/0035345 | A1 | 3/2002 | Beck |

FOREIGN PATENT DOCUMENTS

| | | |
|---|---|---|
| EP | 0927560 | 7/1999 |
| FR | 2773320 | 7/1999 |
| SU | 0654254 | 3/1979 |
| SU | 995783 | 2/1983 |
| SU | 1342500 | 10/1987 |
| WO | 90/11054 | 10/1990 |
| WO | 93/03790 | 3/1993 |
| WO | 00/47274 | 8/2000 |
| WO | 03/030989 | 4/2003 |
| WO | 2004/066980 | 8/2004 |

OTHER PUBLICATIONS

Halhal et al., "Iontophoresis: from the lab to the bed side," Experimental Eye Research, vol. 78, 2004, pp. 751-757.

Silvia Ligorio Fialho et al., "Iontoforese No Transporte Ocular de Drogas," Arq. Bras. Oftalmol., vol. 67, No. 5, pp. 839-845 (2004).

G.A. Kiselev et al., "Procedure for the Administration of Drugs in Gels to Ocular Tissues Through the Use of Electrophoresis" (includes both the Russian-language reference and an English translation thereof).

Ludwig Von Sallmann, "Iontophoretic Introduction of Atropine and Scopolamine Into the Rabbit Eye," pp. 711-719 (1943).

Oleg I. Lebedev, "Electrophoretic Trials in the Early Diagnosis of Primary Glaucoma," pp. 1-18 (1983), (includes both the Russian-language reference and an English language translation thereof).

Francine F. Behar-Cohen et al., "Iontophoresis of Dexamethasone in the Treatment of Endotoxin-Induced-Uveitis in Rats," vol. 65, pp. 533-545 (1997).

Michael Barza et al., "Transscleral Iontophoresis of Gentamicin in Monkeys," Investigative Ophthalmology & Visual Science, vol. 28, No. 6, pp. 1033-1036 (Jun. 1987).

David S. Rootman et al., "Pharmacokinetics and Safety of Transcorneal Iontophoresis of Tobraamycin in the Rabbit," Investigative Opthalmology & Visual Science, vol. 29, No. 9, pp. 1397-1401 (Sep. 1988).

Tim T. Lam et al., "Transscleral Iontophoresis of Dexamethasone," Archives of Opthalmology, vol. 107, pp. 1368-1371 (Sep. 1989).

Robyn E. Grossman et al., "Regional Ocular Gentamicin Levels after Transcorneal and Transscleral Iontophoresis," Investigative Opthalmology & Visual Science, vol. 31, No. 5, pp. 909-916 (May 1990).

Tim T. Lam et al., "A Histopathologic Study of Retinal Lesions Inflicted by Transscleral Iontophoresis," Graefe's Archive for Clinical and Experimental Ophthalmology, vol. 229, pp. 389-394 (1991).

Adam L. Church et al., "An Improved Apparatus for Transscleral Iontophoresis of Gentamicin," Investigative Opthalmology & Visual Science, vol. 33, No. 13, pp. 3543-3545 (Dec. 1992).

Tim T. Lam et al., "Intravitreal Delivery of Ganciclovir in Rabbits by Transscleral Iontophoresis," Journal of Ocular Pharmacology, vol. 10, No. 3, pp. 571-575 (1994).

Sonia H. Yoo et al., "Iontophoresis for the Treatment of *Paecilomyces* Keratitis," Cornea: The Journal of Cornea and External Disease, vol. 21, No. 1, pp. 131-132 (2002).

F. F. Behar-Cohen et al., "Transscleral Coulomb-controlled Iontophoresis of Methylprednisolone into the Rabbit Eye: Influence of Duration of Treatment, Current Intensity and Drug Concentration on Ocular Tissue and Fluid Levels," Experimental Eye Research, vol. 74, pp. 51-59 (2002).

David L. Vollmer et al., "In Vivo Transscleral Iontophoresis of Amikacin to Rabbit Eyes," Journal of Ocular Pharmacology and Therapeutics, vol. 18, No. 6, pp. 549-558 (2002).

Matthew S. Hastings et al., "Visulex: Advancing Iontophoresis for Effective Noninvasive Back-of-the-Eye Therapeutics," Drug Delivery Technology, vol. 4, No. 3, pp. 2-6 (Apr. 2004).

International Search Report, Issued Jun. 28, 2011, from European Patent Application No. EP 11162446.6.

* cited by examiner

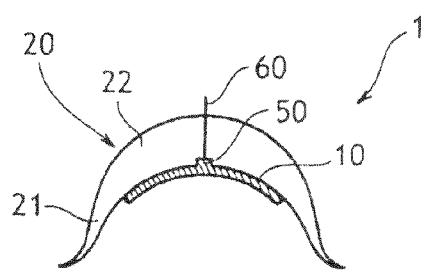
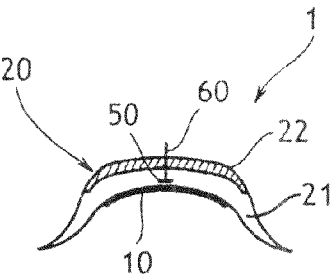
FIG.7a  FIG.7b
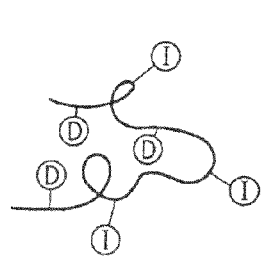
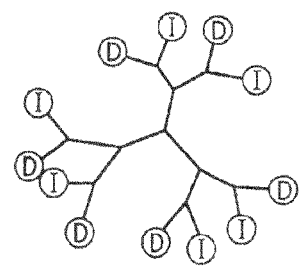
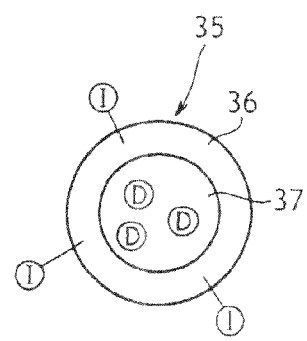
FIG.8a  FIG.8b  FIG.8c
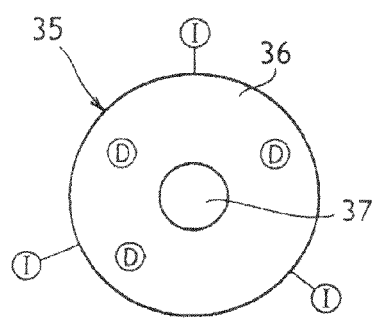
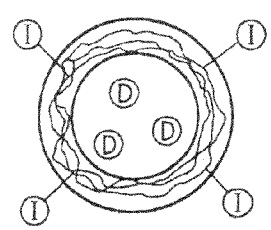
FIG.8d  FIG.8e  FIG.8f

IRRITATION-REDUCING OCULAR IONTOPHORESIS DEVICE

CROSS REFERENCE TO RELATED PATENT APPLICATIONS

This application is a Continuation of U.S. application Ser. No. 13/042,529, filed Mar. 8, 2011, which is a Continuation of U.S. application Ser. No. 12/437,820, filed May 8, 2009, now U.S. Pat. No. 7,937,142, which is a Continuation of U.S. application Ser. No. 11/651,150, filed Jan. 8, 2007, now U.S. Pat. No. 7,548,778, which is a Continuation of U.S. application Ser. No. 10/861,117, filed Jun. 3, 2004, now U.S. Pat. No. 7,164,943, which claims priority under 35 U.S.C. §119 to French Patent Application No. 0404673, filed on Apr. 30, 2004, now French Patent No. 2,869,531, each incorporated herein by reference in their entirety.

BACKGROUND OF THE INVENTION

The present invention relates to an ocular iontophoresis device for delivering medication (into the eye).

The principle of ocular iontophoresis is applying an electric field to an electrolytic substance containing at least one medication, in order to transport the medication(s) into the body or the organ to be treated, via the biological membranes of the eye.

Like the brain, the eye is protected from the central venous system by biological barriers (hemo-ocular, hemo-aqueous, hemo-retinal) making it very difficult to administer medication at sufficient concentration, specifically to the posterior segment of the eye, in particular to the retina.

The systemic path (oral or intravenous) can thus administer only a very small fraction (a few %) of the initial quantity into the internal tissue of the eyes, and thus rapidly becomes insufficient.

That is why techniques of locally administering medication to the eye have been and are being developed, including the following:

- direct injections around the eye (peribulbar, retrobulbar) or into the eye (intraocular), which remain very traumatic. Furthermore, the drug is always diluted rapidly, disappearing from the vitreous humor in a few days, or being rejected systemically. This mode of administration also presents risks of infection, of bleeding, of cataracts, and of detaching the retina. Finally, disorders such as glaucoma cannot be treated in this way because of the increase in intraocular pressure.
- topical applications of drops, which do not treat the posterior segment since penetration is very limited (typically less than 5%) and which do not enable therapeutic concentrations to be reached beyond the anterior segment. In addition, tears wash the drug away quickly, ocular fluids opposing penetration and the diffusion path is then quite long, Applications need to be repeated frequently.
- photodynamic therapy consists in injecting medication systemically and in activating it locally by using a laser at a certain wavelength, taking advantage of the transparency of the cornea. However drawbacks remain: the patient must remain in the dark, the medication must be modified by adding a photosensitive agent which prevents it from acting prior to being activated, and the doctor must possess equipment that is relatively expensive.
- inserts in the form of reservoirs of medication placed on the surface of the eye (in non-invasive manner), such as lenses or preferably in the conjunctival sac, and serving to deliver medication in continuous or programmed manner. Numerous systems have been developed, either in the form of a lens or a ring, or in the form of a small lenticular or tubular reservoir placed in the conjunctival sac. The main drawbacks of these systems are firstly limited passage to the posterior segment which limits their use to pathologies of the anterior segment (inflammation, conjunctivitis), and secondly the risk of the insert being expelled,
- intraocular implants for programmed release of medication are put into place surgically in the vitreous humor like Vitrarest® from Baush & Lomb, possibly fixed to the sclera like the chemical implant coated in a layer of polymer releasing the medication (InnoRx/Surmodic), or else are bioerodable/biodegradable (Surodex® from Oculex, now Allergan). One of the drawbacks of this type of device is that they move freely in the vitreous humor and run the risk of touching the retina, thereby locally increasing the concentration of medication, possibly up to a toxic level. Although it is possible to suture the implant, that requires an incision that is relatively large (5 millimeters (mm)). Another drawback is the need for regular replacement. Finally, it is not possible to interrupt or to accelerate the treatment as a function of how the pathology responds to treatment.

Ocular iontophoresis is another technique for local administration of medication into the eye, and it enables most of the drawbacks of the other techniques mentioned above to the mitigated. It also makes it possible in non-invasive manner to obtain concentrations and residence times in the eye that are equal to or greater than prior techniques.

Iontophoresis devices are typically constituted by a direct current (DC) electric field source coupled to two electrodes referred to respectively as "active" and "passive" electrodes. The active electrode acts on an electrolyte containing the active principle(s), while the passive electrode serves as a return electrode and enables the electric circuit to be looped through the patient's body.

SUMMARY OF THE INVENTION

Instead of using a system of redox reaction metal electrodes where toxic metal particles might pass into solution, it is preferred to use a system of Ag/AgCl electrodes for implementing iontophoresis, on the principle illustrated with reference to FIG. 1. Such iontophoresis is implemented in living tissue 200 via its surface 210, this living surface 210 being in contact firstly with the saline solution of a first compartment (in this case an anode compartment) 1000 containing the active electrode 100 (in this case the anode) made of Ag, and secondly with the saline solution of a second compartment (in this case the cathode compartment) 1100 containing the passive electrode 110 (in this case the cathode) made of AgCl. The cathode compartment 1000 also contains medication D in an ionizable form (thus giving a counter ion A when ionized). The polarizations of the electrodes 100 and 110 then establish electrode migration of ionic species in solution, including the ionized medication, which then passes through the living surface 210, and is thus introduced into the living tissue 200. This iontophoresis thus implies that AgCl becomes deposited on the active electrode 100, and that AgCl decomposes on the passive electrode 110 to form chloride ions in solution. This principle requires the use of medication in solution in salt water, the $Na^+$ and the $Cl^-$ ions then competing with the medication, thereby significantly reducing the efficiency of the iontophoresis.

Although iontophoresis has been used clinically to deliver medication in dermatology for several decades, it is a technique that is still relatively recent in opthalmology.

Since the eye is an organ that is extremely different from, and is much more fragile in many aspects (such as the transparency of the cornea, the sensitivity of the mucus membrane, . . . ) than most other parts of the animal body, ocular iontophoresis presents technical specificities that are very different from those of other types of iontophoresis (current, current density, duration and control of the electric field to be applied, leakage currents due to the presence of lachrymal liquid (known as the "arc effect"), particular vigilance concerning the doses of the chemical species to be administered and the presence of contaminants in solution, special attention to electrochemical phenomena that take place in solution during electrolysis, etc.).

There therefore remains a need to improve the effectiveness of delivery in order to reduce the risks of burning and poisoning tissue, and of irritating tissue in general (erythema) which can limit the use of ocular iontophoresis.

An improvement in ocular iontophoresis could be found in:
  applying the electric field preferentially to the sclera rather than to the cornea, in particular in order to protect the very fragile surface of the cornea that participates directly in vision;
  minimizing the density of the electric field (ratio of current over area), i.e. by maximizing the application area and the electrode area;
  controlling the applied electric field intensity more accurately, thus achieving good reproducibility;
  limiting application time to enable lachrymal fluid to circulate well; and
  facilitating the passage of ions into the eye.

Document FR 2,773,320 discloses an iontophoresis device for delivering medication around the cornea, the device comprising a medication reservoir having a surface active electrode of conductive material which specifically provides the above-mentioned advantages. Mainly by presenting a surface active electrode that is situated at a determined distance from the eye, that device thus makes it possible to distribute the electric field in fairly uniform and constant manner over its application surface.

However, when using the above advanced device, it has been found in clinical trials that although ocular irritation is indeed reduced, it nevertheless remains present. The results of such experiments are described in "Iontophoresis: from the lab to the bedside" by Halhal et al. In "Experimental Eye Research" 78 (2004) 751-757.

In addition, it would be desirable to further reduce the time required for implementing iontophoresis, in order to reduce potential risks during implementation and in order to improve patient comfort.

An object of the invention is to reduce the risk of eye irritation compared with the state of the art.

Another object of the invention is to provide an ocular iontophoresis device that is capable of operating with solutions, such as saline solutions, that contain few or no ions competing with the ionized medication, thus achieving greater delivery of medication for given electric field.

Another object is to achieve the above object while not significantly reducing the intensity and the uniformity of the electric field applied to the electrolytic solution, thus making it possible to administer the medication in uniform manner, and significantly to reduce the time required for implementing iontophoresis (and thus reduce the risks associated therewith).

Another object is to propose an ocular iontophoresis device that withstands the pressure exerted by the eyelids when they close.

Another object is to propose an ocular iontophoresis device containing a medication that is presented in a form that is more easily ionizable.

Thus, in a first aspect, there is provided an ocular iontophoresis device for delivering medication, the device comprising a medication reservoir suitable for being positioned on the eye, at least one medication in solution in the reservoir, an active electrode disposed in the reservoir, and a passive electrode, the reservoir including at least one medication dissolved in non-saline water, the solution that contains it having a pH lying in the range 6.5 to 8.5, the medication(s) having a pKa lying in the range about 5.5 to about 9.5 and each includes an active principle which is associated with an additive, such as a dendrimer, a polymer, a nanoparticle, a microsphere, a liposome, or an emulsion, and having an ionic form of valency greater than or equal to 1.

There is also provided a method of treatment by ocular iontophoresis, in which, in order to deliver medication, an iontophoresis device is positioned on the eye, the device comprising a reservoir of medication in solution, an active electrode placed in the reservoir, and a passive electrode, and in which ocular iontophoresis is implemented by means of the device, the medication(s) being dissolved in non-saline water, the solution that contains it having a pH lying in the range 6.5 to 8.5, the medication(s) having a pKa lying in the range about 5.5 to about 9.5 and including an active principle which is associated with an additive such as a dendrimer, a polymer, a nanoparticle, a microsphere, a liposome, or an emulsion, and having an ionic form of valency greater than or equal to 1.

Furthermore, in a third aspect that is independent and possibly also complementary, there is provided an ocular iontophoresis device including an active electrode comprising an electrically conductive layer arranged to receive an electric field suitable for polarizing it sufficiently to electrolyze the medication(s) in solution, and also comprising a protective layer situated between the conductive layer and the solution, said protective layer reacting significantly less than the conductive layer during electrolysis in the solution in question.

BRIEF DESCRIPTION OF THE DRAWINGS

Other characteristics, objects, and advantages of the invention appear better on reading the description below, which is illustrated by the following figures:

FIGS. 7a and 7b show different shapes for the rigid or reinforced portion of the reservoir of an ocular iontophoresis device of the invention; and FIGS. 8a to 8f show different molecules binding different additives to the medication for administration.

DETAILED DESCRIPTION OF THE PREFERRED EMBODIMENTS

Figure 1:
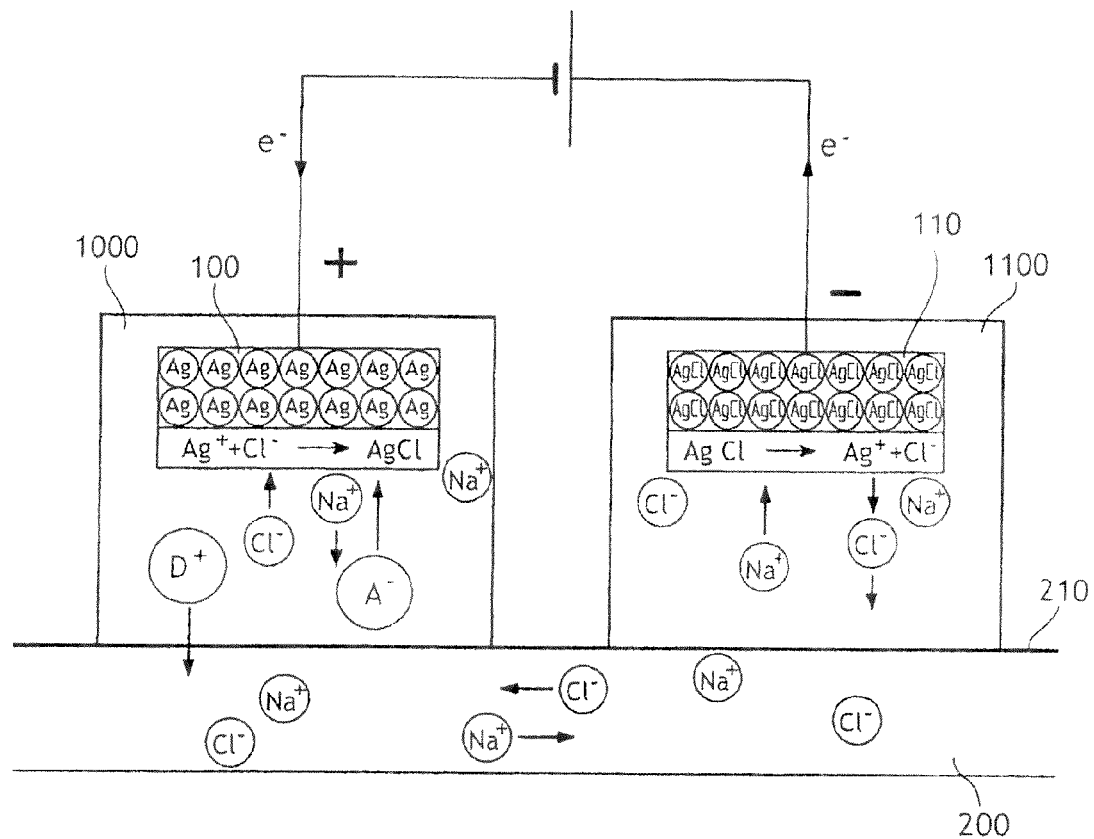
FIG. 1 is a diagram showing the principle of iontophoresis in the prior art.
Figure 2:
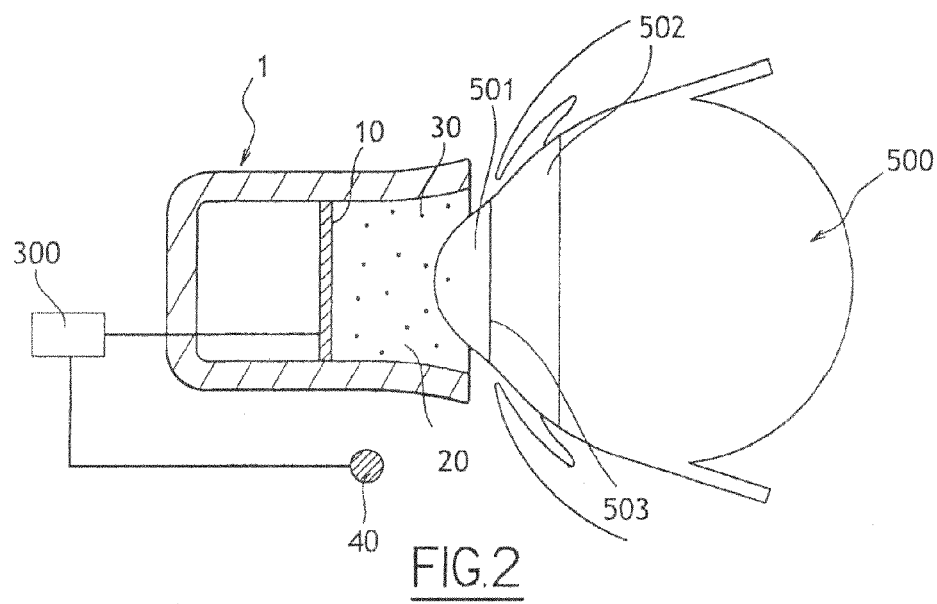
FIG. 2 is a diagram showing an example of an ocular iontophoresis system.

With reference to FIG. 2 there is shown very diagrammatically an ocular iontophoresis system comprising an iontophoresis device 1 including an active electrode 10, a reservoir 20, and at least one medication 30 stored in the reservoir 20, a passive electrode 40 enabling the electric circuit to be looped, and an electrical power supply 300 delivering DC to the electrodes 10 and 40.

The active electrode 10 is disposed in the reservoir 20 either by being fitted thereto or by being formed therein directly (e.g. by electro-plating).

The reservoir 20 is made of an electrically insulating material, such as a plastics material, a silicone material, a polymer, or any other material of this type.

At least one medication 30 is placed in a gel or in solution, and is itself ionizable or is in a form that facilitates ionization (appropriate additives).

By medicament is meant any substance or composition that may be used on or administered to humans or animals as an aid in the diagnosis, treatment or prevention of disease or other abnormal or cosmetic condition or for the relief of pain or to control, diagnose or improve any physiologic or pathologic condition.

The passive electrode 40 may be placed on a portion of the body (in order to "loop" current through the body), for example on an ear, the forehead, or a cheek.

The device 1 is placed on the eyeball 500, optionally being inserted under the eyelids.

The dimensions of the device 1 may be adapted to the size of the eyeball 500, it being understood that the size of the human eye increases rapidly during the first three years of life, with its diameter going from 16 mm to 23 mm (anteroposterior), and that an adult human eye has a volume of 5.5 ml and an anteroposterior diameter of 24 mm.

Nevertheless, given that the dimensions of eyes are remarkably stable in the human population and independent of variations in body size or of race, and that eyes reach their mature size quite early, it is possible to select universal dimensions for the device 1.

The device 1 may be adapted to administer the medication(s) 30 via:
the cornea 501 alone; or
both the sclera 502 and the cornea 501; or
the sclera 502 alone.

The cornea 501 constitutes about 5% of the total area of the eye (cornea 1 square centimeter ($cm^2$) and sclera 17 $cm^2 \pm 1.5$ $cm^2$) and joins the sclera 502 at the limbus 503. In the human being, the diameter of limbus 503 is 11.7 mm.

The cornea 501 is a non-vascular transparent tissue, and in man its radius of curvature is 7.8 mm, its thickness is 0.7 mm in the centre and 0.5 mm at the periphery, and it is situated in front of the functional retina. It is made up of three layers (the epithelium, the stroma, the endothelium) one of which (the epithelium) is generally the limiting factor, since it constitutes a barrier encouraging lipophilic substances and excluding practically all macromolecules of size greater than 10 angstroms (Å).

The sclera 502 is tissue that is elastic and microporous, containing 70% water, it covers practically all the remainder of the surface of the eye, and it has mean thickness of 0.53 mm±0.14 mm at the corneo-scleral limbus 503. Thereafter, its thickness decreases to 0.3 mm±0.17 mm at the equator, after which it increases progressively to 0.9 mm to 1.0 mm at the optic nerve. It includes the conjunctiva which is a fine and vascularized mucus membrane. The particle size exclusion limit lies in the range 20,000 daltons (Da) to 150,000 Da.

For the sclera 502, the factor limiting the passage of molecules is more the size of the molecules than their lipophilicity.

The sclera 502 is more permeable than the cornea.

Present opinion concerning the tolerance of the sclera 502 and of the cornea 501 respectively to current density is respectively 100 milliamps per square centimeter ($mA/cm^2$) and 20 $mA/cm^2$.

There follows a comparison of the physical and biological magnitudes associated with the cornea 501 and with the sclera 502:

|  | Cornea | Sclera |
|---|---|---|
| Minimum thickness (mm) | 0.5 | 0.39 |
| Maximum thickness (mm) | 0.7 | 1.0 |
| Surface area ($cm^2$) | 1 | 16.3 |
| Maximum size of the molecules 1,000 150,000 (Da) | 1,000 | 150,000 |
| Maximum current density 20 100 ($mA/cm^2$) | 20 | 100 |

In a preferred variant of the invention, it is possible to dispense the medication(s) 30 through the sclera 502, it being understood that it presents characteristics that encourage iontophoresis (greater permeability, greater surface area for administration, more favorable to the application of high currents) and that the cornea is a portion of the eye that is much more critical than the sclera 502.

In this particular variant, a special device 1 is provided enabling the medication(s) to be administered through the sclera 502, and solely through the sclera 502, such as a device 1 close to that described in document FR 2,773,320, i.e. comprising:
an active electrode 10 that is annular so as to be suitable for being positioned facing the sclera 502; and
a reservoir 20 formed by an outer side wall and an inner side wall so that the active electrode 10 can be contained between them, the end wall of the reservoir being the active electrode 10 or a transverse wall connecting one end of the outer side wall to one end of the inner side wall.

In another variant, the active electrode 10 is not annular, and the reservoir 20 has a single outer side wall so that the active electrode 10 can be contained in the reservoir 20, the reservoir being closed at one end either by a transverse wall forming an end wall of the reservoir, or by the active electrode 10 (which amounts to a reservoir as shown in FIG. 2).

Figure 3:
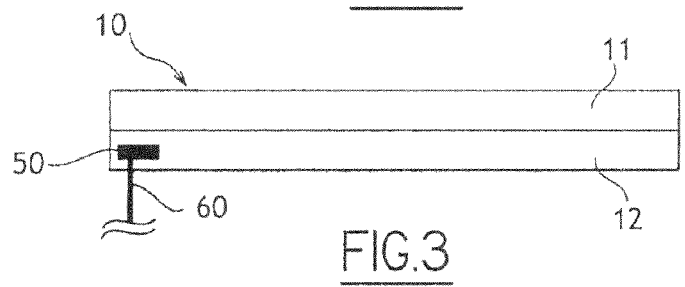
FIG. 3 shows an active electrode of an ocular iontophoresis device of the invention.

With reference to FIG. 3, there is shown an active electrode 10 of the invention comprising the following two layers:
an electrically conductive layer 12 arranged so as to receive an electric field suitable for polarizing it sufficiently to electrolyze the medication(s) in solution in the reservoir 20 (not shown in this figure); and
a protective layer 11 secured to the conductive layer 12, the protective layer 11 reacting significantly less than the conductive layer 12 during electrolysis in the solution under consideration.

An electrical connection 50 is provided on the conductive layer 12 (e.g. by soldering) thereby enabling an electrical link 60 to be connected to the active electrode 10.

The material which constitutes the protective layer 11 is selected in particular to oxidize or erode little or not at all during electrolysis, while nevertheless being sufficiently conductive to avoid excessively reducing the application of the electric field delivered by the conductive layer 12.

By way of example it is possible to select the material containing at least some carbon, such as, for example, an intrinsically conductive polymer such as polyacetyline or a polyaniline or a polypyrrole or a polyphenylene or a polythiophene or a polymer filled with carbon black; or a carbon fiber; or a graphite; or a diamond-like carbon (DLC).

For example, it is possible to select a semiconductor material.

The protective layer 11 is of a thickness lying, for example, in the range 0.1 nanometers (nm) to 0.5 millimeters (mm) approximately.

The conductive layer 12 may be made of any material which is a good conductor, such as a metal, e.g. silver.

The conductive layer 12 may be of a thickness lying in the range 0.1 nm to a few mm.

The protective layer 11 advantageously covers the entire conductive layer 12.

Once the active electrode 10 has been placed in the reservoir, the protective layer 11 advantageously covers the entire end wall of the reservoir.

This type of electrode 10 serves to increase the efficiency of iontophoresis compared with:
- an electrode made solely of carbon (since carbon is not sufficiently conductive, thereby not providing sufficient uniformity of current when fed locally, and leading to non-uniform administration of medication, particularly in the target tissues, i.e. the circular immediate vicinity of the cornea-several limbus 503), since in this case the conductive layer 12 guarantees high current density and good current uniformity because of its high electrical conductivity; and
- an electrode of Ag or of AgCl since, in this case, the solution is not necessarily saline (as is the case with Ag/AgCl electrodes), which implies a reduction in competition between the medication(s) and ions of sodium and of chlorine.

The increase in the efficiency of iontophoresis is highly beneficial since it enables application time to be reduced. In ocular iontophoresis, it is important to comply with application times that are very limited, typically being about 3 minutes (as recommended in patent FR 2,773,320), since a longer application time runs the risk of significantly disturbing the physiological role of the lachrymal film in hydrating the ocular mucus membranes, running the risk of significant corneal inflammation. In addition, this reduction in application time diminishes patient discomfort.

Furthermore, the protective layer 11 is not made of a material that is oxidizable at the current levels used, and therefore does not generate potentially toxic ions (such as metal particles that might, for example, disturb the operation of the retina or irritate the conjunctiva).

In addition, the active electrode 10 of the invention does not use any noble material such as gold or platinum, thus making it less costly. In this context, the Applicant has found during clinical trials, that using gold as the passive electrode 40 still gives rise to an oxidation reaction, as is not the case when the passive electrode 40 is made of carbon.

The active electrode 10 of the invention is also applicable to lipophilic medication, unlike an active electrode made of Ag/AgCl for which chorine and sodium ions exist only in aqueous form.

The protective layer 11 on the electrode thus provides a perfect interface with the medication contained in the reservoir of the device.

The active electrode 10 of the invention is of a shape that is adapted to the surface of the eye that is to be treated.

The dimensioning and the shape of the active electrode 10 are thus arranged in such a manner that its projection covers at least a portion of the cornea 501, or at least a portion of the cornea 501 together with at least a portion of the sclera 502, or at least a portion of the sclera 502.

The third option is preferred because of the advantages achieved by iontophoresis through the sclera 502, as described above.

In a first configuration, it may be decided to make the active electrode 10 by coating a conductive wire (in this case representing the conductive layer 12) with a material that reacts significantly less than does the material of the conductive wire during electrolysis of the solution in consideration, thus forming the protective layer 11 on the conductive layer 12.

Such an active electrode 10 can thus be made from a conductive wire made of silver and a protective layer made of carbon.

One possible architecture for such an active layer would be an array of wires, each made as described above (a covered conductor wire) of a consistency that resembles a fabric, with the cores of the fibers (or of the wires) being fed with electricity.

In the second configuration, a surface active electrode 10 is selected so as to distribute current density more uniformly over the surface to be treated.

Figure 4A:
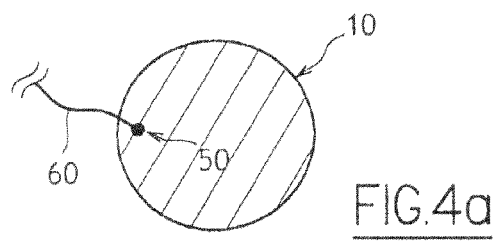
FIGS. 4a to 4f show different forms of active electrode for an ocular iontophoresis device of the invention.
Figure 4B:
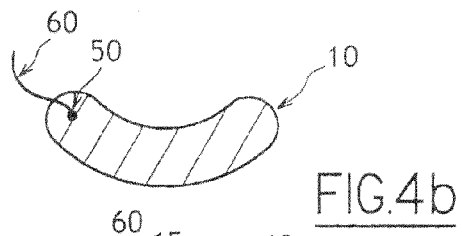
Figure 4C:
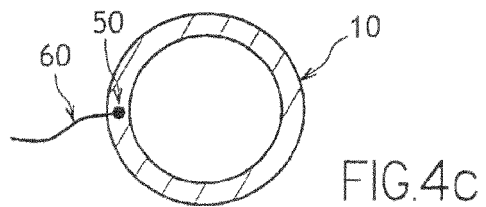

FIGS. 4a to 4f show particular shapes which may be given to a surface electrode of the invention, such as a disk shape or an ellipse (FIG. 4a) or a shape constituting a portion of a ring (FIG. 4b) or an entire ring (FIG. 4c).

Figure 4D:
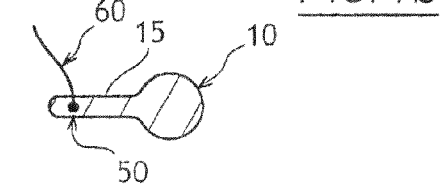
Figure 4E:
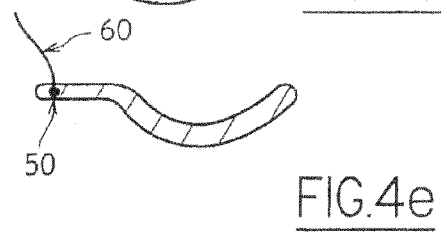

With reference to FIGS. 4d and 4e, a wire link 60 is provided for electrically connecting the active electrode 10 to a suitable electrical power supply (not shown), the wire link 60 being connected electrically at 50 to the active electrode locally via the conductive layer 12. In this case, the connection 50 is made by means of an offset part 15 that is offset from the active electrode 10 so as to located outside the reservoir (once the electrode has been placed therein), one end of the offset part 15 being electrically connected to the conductive layer 12 of the active electrode 10, while the other end of the offset part receives the wire link 60. The connection 50 can thus the offset from the reservoir, thereby avoiding the harmful effects that might arise from the electrical connection (heat being given off, local leakage currents, . . . ).

Figure 4F:
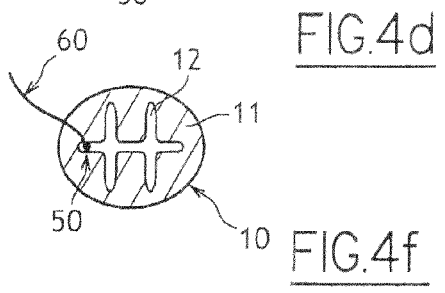

With reference to FIG. 4f, the conductive layer 12 is in the form of a grid or array.

Optionally, the active electrode 10 is sufficiently flexible to be able to deform under the action of mechanical forces of the kind that are exerted while pressing the device against the eye.

The active electrode 10 is advantageously arranged, in operation, to present current density of about 10 mA/cm$^2$, and to be polarized for about 10 minutes.

The active electrode 10 may be placed against the end wall of the reservoir 20.

The active electrode 10 may be formed directly on the end wall of the reservoir. For this purpose, it is possible to use one of the following techniques:
- electroplating to form the conductive layer, followed by projecting particles to form the protective layer;
- successively depositing an ink filled with an electrically conductive material in order to form the conductive layer, and then an ink filled with a material that is less electrically conductive to form the protective layer;
- successively depositing a solid film filled with an electrically conductive material to form the conductive layer, and then a solid film filled with a material that is less electrically conductive to form the protective layer; and successively overmolding polymers filled respectively with an electrically conductive material to form conductive layers, and polymers filled with a material that is less electrically conductive to form protective layers.

Figure 5:
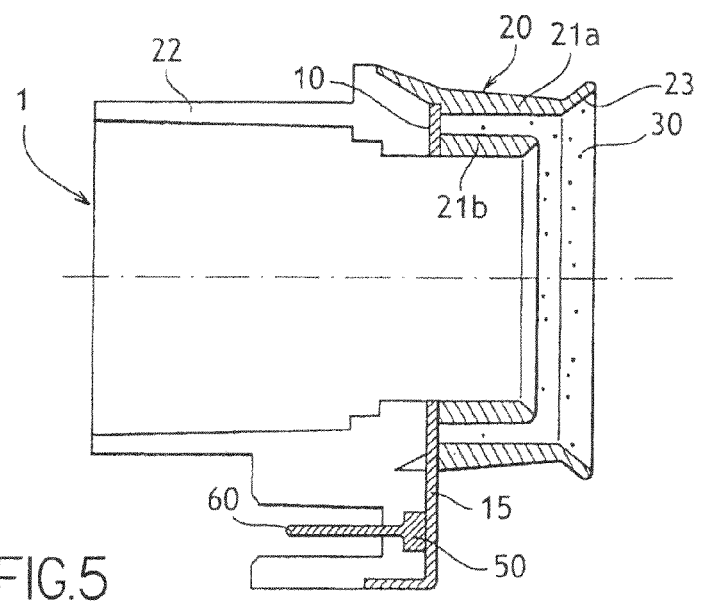
FIG. 5 shows an ocular iontophoresis device of the invention.

With reference to FIG. 5, there can be seen an ocular iontophoresis device 1 in which the active electrode 10 presents a through opening so as to provide an annular structure, and is placed at the end of the reservoir 20, which is also annular in shape.

The device 1 is advantageously arranged in such a manner that the active electrode 10 is situated about 4 mm from the surface of the eye when the device 1 is in operation, the current of the active electrode 10 of the invention not exceeding 10 mA/cm$^2$, and the application time not exceeding 10 minutes.

The active electrode 10 includes an offset portion 15 enabling the connection 50 with the wire link 60 that supplies electricity to be offset out from the reservoir (and thus out from the solution containing the medication(s) 30), as already mentioned above (with reference to FIGS. 4d and 4e).

The reservoir 20 includes an outer side wall 21a and an inner side wall 21b enabling the active electrode to be contained between them.

The free end of the inner side wall 21b is optionally slightly offset relative to the free end of the outer side wall 21a such that the opening of the reservoir 20 (between these free ends) thus defines a concave curved surface that is substantially complementary in shape to the convex curved shape of the surface of the eye.

One end of the outer side wall 21a may be connected to one end of the inner side wall 21b by a transverse wall forming an end wall of the reservoir. The active electrode 10 is then positioned or formed on said end wall of the reservoir.

In a variant, the active electrode 10 is positioned or formed between the side walls 21a and 21b of the reservoir in such a manner as to constitute the end wall of the reservoir.

The inner side wall 21b of the reservoir 20 optionally presents a mean inside diameter $d_i$ such that $D<d_i \leqq 1.2\,D$, D being the diameter of a cornea 501.

In which case, iontophoresis takes place exclusively through the sclera 502.

The outer side wall 21a of the reservoir 20 optionally presents a mean outside diameter $d_e$ where $1.4\,D<d_e \leqq 1.8\,D$.

In another aspect of the invention, and still with reference to FIG. 5, the side walls 21a and 21b of the reservoir 20 are sufficiently flexible to take up the shape of the surface of the eye.

In addition, the reservoir 20 has a rear portion 22 that is reinforced or rigid and that is suitable for withstanding sufficiently the pressure exerted by the eyelids.

In this case, the active electrode 10 is interposed between these two portions of the reservoir 20, resting against the rigid rear portion 22.

Thus, when the reservoir 20 is in position, the distance between the surface of the active electrode 10 and the surface of the eye can be maintained more less constant in spite of the mechanical stresses exerted by the eyelids.

The ring formed by the active electrode 10 must keep its shape under the pressure exerted by the eyelids, thereby maintaining the application area and also the distance of about 4 mm relative to the tissue to be treated (see above), since otherwise there would be a danger of a short-circuit by favorable lines of current being established between the active electrode 10 and the tissue.

The flexible outer side walls may also act as a barrier against external contaminants and lachrymal liquid that might disturb the operation of the device 1 (arc effect). These flexible side walls thus form a barrier to current leaking from the reservoir 20 and/or against intrusion of external contaminants into the reservoir 20.

The flexible side walls 21a and 21b may be made of silicone, a material that is highly suitable for making contact with the eye.

However its flexibility certainly does not enable it to keep its shape in geometrically accurate manner.

That is why it is appropriate for the rigid or reinforced rear portion 22 to be made of a material such as, for example, polymethyl methacrylate (PMMA), or silicone of the polydimethyl siloxane type (PDMS).

PMMA is a rigid material suitable for keeping the active electrode 10 in shape. However it is unsuitable for making the flexible side walls 21a and 21b (it is a material that is too traumatic for the delicate mucus membrane of the eye).

These two materials in combination thus provide a device structure that is entirely suitable for ocular iontophoresis.

The rigid portion 22 of the reservoir 20 can be made, for example, by machining, molding, vacuum casting, or any other method suitable for working polymer materials of rigid or semi-rigid kind such as polystyrene (PS), acrylonitrile-butadiene-styrene (ABS), polyethylene (PE), polypropylene (PP), polyamide (PA), polycarbonate (PC), PMMA, polyurethane (PUR), . . . etc.

During fabrication of the part, provision can be made to mold means for filling the reservoir 20 with medication(s) 30 and/or means for circulating the medication(s) 30 in the reservoir 20. For example, tubes for feeding the medication 30, and optionally outlet tubes for the medication(s) 30 may be provided.

The active electrode 10 made of a layer of conductive material 12 and a layer of protective material 11 can then be deposited on the surface of the part forming the end wall of the medication reservoir, using one of the methods mentioned above.

Finally, the flexible portions 21a-21b can be made of a polymer material such as, for example, an elastomer polymer of the PUR type, polyether block amide (PEBA), silicone (SI), or styrene-ethylene-butadiene-styrene (SEBS), and it may be fitted to the assembly using any suitable method, for example adhesive, heat sealing (e.g. by ultrasound, or by rotation, or by mirror), or by overmolding.

The flexible portions 21a-21b of the reservoir 20 may also be made by successively adding sections of material of progressively-varying hardness, from the thickest to the thinnest and from the stiffest to the most flexible, so as to make a reservoir of stiffness that increases progressively going away from the surface to be treated (see below).

The inside walls of the reservoir 20 are optionally provided so as to define compartments, the active electrode 10 then being subdivided into active electrode portions, each active electrode portion being suitable for being placed in its own compartment. Specific treatments can then be performed using different medications 30, each occupying a different compartment, and administered simultaneously or in deferred manner (in which case each electrode portion has its own current control). Advantageously, filling and/or circulation means for medication 30 are provided in each compartment.

In a particular aspect of the invention, the flexible side walls 21a and 21b of the reservoir 20 are progressively more rigid on going progressively further away from the application surface of the device 1 in operation (i.e. going away from the opening of the reservoir 20).

With reference to FIGS. 6a to 6d, several examples are shown of such side walls 21 of increasing rigidity, each of section that becomes progressively larger and larger on going away from the opening of the reservoir 20.

Figure 6A:
FIGS. 6a to 6d show different shapes for the flexible portion of the reservoir of an ocular iontophoresis device of the invention.

With reference to FIG. 6a, the side wall 21 thus forms a ramp sloping progressively away from the opening of the reservoir 20.

Figure 6B:

With reference to FIG. 6b, the side wall 21 thus form is a lip of section that increases going away from the opening of the reservoir 20, and of sides that are concave.

Figure 6C:

With reference to FIG. 6c, the side wall 21 is thus constituted by successive layers of ever increasing section (on going away from the opening of the reservoir 20). These various layers may optionally be of ever increasing hardness.

Figure 6D:
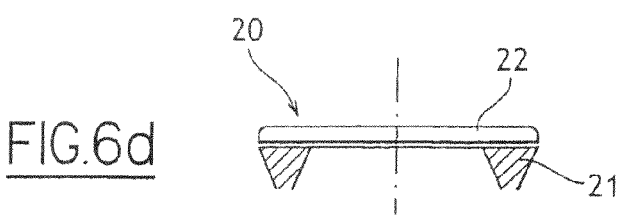

With reference to FIG. 6d, there is shown a reservoir 20 of side walls 21 of rigidity that increases going away from the opening of the reservoir 20, and having a rigid portion 22 that closes the reservoir 20 at one end, also providing it with reinforcement against mechanical forces from the eyelids.

Variants of the rigid or reinforced portions 22 of a reservoir 20 are shown with reference to FIG. 7a.

In FIG. 7a, the device 1 has a reservoir 20 constituted in this case by a compact unit including a fine (flexible) portion forming lips 21 for putting into contact with the eyeball 500, and a thicker (rigid) rear portion 22 for opposing the forces exerted by the eyelids closing. The overall shape of the active electrode 10 is curved, with an inside radius of curvature close to the radius of curvature of the cornea 501. The active electrode 10 is placed in the hollow of the reservoir 20.

With reference to FIG. 7b, the device 1 is substantially identical to that of FIG. 7a, with the exception that in this case the rigidity of the rear portion 22 is provided by adding new, harder material that reinforces the device.

Another aspect of the invention relates to the content of the reservoir 20, specifically the medication(s) 30, and the form that can be taken on to encourage administration into the tissue of the eye, and more particularly into the retina.

In opthalmology, examples of medications that might be concerned by this mode of administration are as follows: anti-inflammatory agents (dexamethazone, methylprednisolone hemisuccinate, betamethasone, triamcinolone, . . . etc.); antiallergy agents; anti-glaucoma agents; antiangiogenic agents and substances acting on the neovascular endothelium (retinoblastoma, age-related degenerative diseases of the retina, diabetic retinophatias); antibiotics; antifungal agents; antiviral agents; neuroprotectors.

Furthermore, numerous molecules are being developed to slow down or even stop the neovascularization that is observed in degenerative pathologies of the retina. These molecules can likewise be transferred by iontophoresis, and thus come within the ambit of the invention.

In addition, certain substances may also facilitate diagnosing diseases of a proliferative nature or the consequences of diabetes. Diagnosis is presently performed by systemic injection of fluoresceine, enabling the state of the tissue in the anterior segment of the eye to be diagnosed visually. It is also possible to administer these substances by iontophoresis.

The electro-migration that occurs during iontophoresis relates to transporting charges and depends on the valency of the substance.

For Hydro-Soluble Medication

It is preferable to ensure that a charged species is present in solution, depending on the dissociation relationship.

In practice, the eye is capable of withstanding a fairly wide pH range of 4.5 to 11.5, with this being possible because of the lachrymal liquid (pH of about 7.4) buffer system washing the surface of the eye.

Nevertheless, any application of a device on the surface of the eye has the effect of limiting this mechanism very strongly.

In practice, it is therefore preferable for the pH of the solution to lie in the range about 6.5 to about 8.5.

Consequently, if the acid dissociation constant pKa of the medication is not greater than these values, or if the basic dissociation constant pKb is not less than these values, the proportion of ionized species in solution will be a small.

Medications should therefore be selected that have pKa lying in the range about 5.5 to about 9.5.

It is then possible to use an acid or a basic form of the medication for administration or to bond the active molecule (also called the active principle) (written "D") to an additive presenting terminating ions (and to a ligand, written "I", electrically neutralizing the combination), such as a polymer (see FIG. 8a), a dendrimer (see FIG. 8b), a polymer nanoparticle or a microsphere (see FIG. 8e), or a liposome (with reference to FIG. 8c, the medication is then contained in the aqueous core 37 and not in the wall 36 of the liposome 35).

With reference to FIG. 8f, the medication can also be modified, so as to present a structure that is intermediate between the active molecule D and the ligand I.

For Lipophilic Medication

It is usually possible to reformulate the medication in the form of an anionic or a cationic emulsion (the medication is then dissolved in the oil phase of an oil-in-water emulsion) or in the form of liposomes (with reference to FIG. 8d, the medication is then contained in the wall 36 of the liposome 35, and no longer in the aqueous core 37), likewise positively or negatively charged.

For Neutral Medication

It is possible to benefit only from the electro-osmosis mechanism. Under such second senses, it is preferable to use an ionized form of the active molecule, such as Dexamethasone phosphate, rather than Dexamethasone which is neutral in solution.

Finally, the concentration of substance should be as high as possible, the only limiting factor being solubility and tolerance by the eye, e.g. the maximum molecular weight of particles for administration that can be accepted by the membrane of the sclera, or the irritation of the mucus membrane as generated by making contact with the substance.

What is claimed is:

1. An ocular iontophoresis device for delivering medication to an eye, comprising;
   a reservoir, the reservoir having a proximal end and a distal end, the proximal end comprising a flexible lip configured to engage the eye for delivery of the medication;
   an active electrode disposed in close proximity to the distal end of the reservoir, the active electrode is curved having an inside radius of curvature close to the radius of curvature of a cornea of the eye; and
   a medication stored in the reservoir.

2. The ocular iontophoresis device of claim 1, the active electrode comprising:
   an electrically conductive layer; and
   a protective layer coupled to the electrically conductive layer, the protective layer reacting significantly less than the conductive layer during iontophoretic delivery of the medication.

3. The ocular iontophoresis device of claim 2, wherein the medication is stored between the protective layer and the proximal end of the reservoir.

4. The ocular iontophoresis device of claim 2, wherein the protective layer comprising:
   a material that erodes little or not at all during iontophoretic delivery of the medication and is sufficiently conductive to avoid excessively reducing the application of an electric field delivered by the conductive layer.

5. The ocular iontophoresis device of claim 4, wherein the material comprising:
   at least one of a polyacetyline, a polyaniline, a polypyrrole, a polyphenylene, a polythiophene, a polymer filled with carbon black, a carbon fiber, a graphite, and a diamond-like carbon.

6. The ocular iontophoresis device of claim 2, wherein the protective layer substantially covers the electrically conductive layer.

7. The ocular iontophoresis device of claim 1, wherein the active electrode is positioned or formed on the distal end of the reservoir.

8. The ocular iontophoresis device of claim 1, wherein the medication is comprised in a gel or a solution.

9. The ocular iontophoresis device of claim 1, wherein the further comprising a reinforced member coupled to opposite side of the distal end of the reservoir.

* * * * *